United States Patent
Sugiyama et al.

(10) Patent No.: US 9,268,039 B2
(45) Date of Patent: *Feb. 23, 2016

(54) RADIATION IMAGE ACQUISITION DEVICE (75) Inventors: Mototsugu Sugiyama, Hamamatsu (JP);
Toshiyasu Suyama, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 228 days.

This patent is subject to a terminal disclaimer.

(21) Appl. No.: 13/981,490

(22) PCT Filed: Oct. 21, 2011

(86) PCT No.: PCT/JP2011/074331
§ 371 (c)(1),
(2), (4) Date: Oct. 1, 2013

(87) PCT Pub. No.: WO2012/101881
PCT Pub. Date: Aug. 2, 2012

(65) Prior Publication Data
US 2014/0016754 A1    Jan. 16, 2014

(30) Foreign Application Priority Data
Jan. 25, 2011 (JP) .............................. P2011-013201

(51) Int. Cl.
*G01N 23/04* (2006.01)
*G01T 1/20* (2006.01)

(52) U.S. Cl.
CPC .............. *G01T 1/2002* (2013.01); *G01N 23/04* (2013.01); *G01T 1/20* (2013.01)

(58) Field of Classification Search
CPC ..... G01N 23/223; G01N 23/06; G01N 23/18; G01N 23/043; G01N 23/04; A61B 6/485; A61B 6/482; A61B 6/4225; H04N 5/32
USPC .................. 378/44, 51, 58, 62, 98.3, 98.9
See application file for complete search history.

(56) References Cited

U.S. PATENT DOCUMENTS

| 4,578,803 | A  | 3/1986 | Macovski |
| 5,864,146 | A  | 1/1999 | Karellas |
| 7,405,406 | B1 | 7/2008 | Nagarkar et al. |

FOREIGN PATENT DOCUMENTS

| JP | S63-079043 | 4/1988 |
| JP | H5-152391  | 6/1993 |

(Continued)

OTHER PUBLICATIONS

U.S. Appl. No. 13/981,372, Mototsugu Sugiyama et al.

(Continued)

*Primary Examiner* — Jurie Yun
(74) *Attorney, Agent, or Firm* — Drinker Biddle & Reath LLP (57) ABSTRACT

A radiation image acquisition device includes: a radiation source which emits radiation; a wavelength conversion member of a flat plate shape which generates scintillation light according to incidence of the radiation emitted from the radiation source and transmitted by an object; first imaging means which condenses and images the scintillation light emitted from an entrance surface for the radiation in the wavelength conversion member in a direction inclined with respect to a direction of a normal to the entrance surface; and second imaging means which condenses and images the scintillation light emitted from a surface opposite to the entrance surface in the wavelength conversion member in a direction inclined with respect to a direction of a normal to the opposite surface.

17 Claims, 7 Drawing Sheets

(56) References Cited

FOREIGN PATENT DOCUMENTS

| JP | H5-312734 | 11/1993 |
| JP | 7-27866 A | 1/1995 |
| JP | H8-061941 | 3/1996 |
| JP | 2000-510729 A | 8/2000 |
| JP | 2000-298198 A | 10/2000 |
| JP | 2001-004561 | 1/2001 |
| JP | 2005-207827 A | 8/2005 |
| JP | 2007-155653 A | 6/2007 |
| JP | 2007-327967 | 12/2007 |
| JP | 2008-164429 | 7/2008 |

OTHER PUBLICATIONS

U.S. Appl. No. 13/981,469, Mototsugu Sugiyama et al.
U.S. Office Action dated May 19, 2015 that issued in U.S. Appl. No. 13/981,372 including Double Patenting Rejections on pp. 2-5.
U.S. Office Action dated May 28, 2015 that issued in U.S. Appl. No. 13/981,469 including Double Patenting Rejections on pp. 2-5.

RADIATION IMAGE ACQUISITION DEVICE

TECHNICAL FIELD

The present invention relates to a radiation image acquisition device.

BACKGROUND ART

There is the conventionally known apparatus for applying X-rays emitted from an X-ray source and transmitted by an imaging object, onto a scintillator of a flat plate shape, detecting visible light (scintillation light) generated in the scintillator, by solid-state photodetectors laid on both surfaces of the scintillator, and superimposing image signals from the respective solid-state photodetectors on each other to acquire a radiation image, as described in Patent Literature 1 below. In this apparatus, the photodetector elements are coupled to the X-ray entrance surface and to the back surface behind it in the scintillator and the visible light is detected by each of the entrance-surface-side photodetector element and the back-surface-side photodetector element, thereby increasing efficiency of detection of the visible light.

CITATION LIST

Patent Literature

Patent Literature 1: Japanese Patent Application Laid-open No. H07-27866

SUMMARY OF INVENTION

Technical Problem

The apparatus for detecting the scintillation light on the both surfaces of the scintillator as described above can acquire radiation images in different energy bands on the entrance surface side and on the back surface side behind it, so as to enable acquisition of so-called dual-energy images In the foregoing conventional apparatus, however, the radiation transmitted by the object passes through the entrance-surface-side photodetector element to reach the scintillator, and for this reason, radiation in a relatively low energy band is absorbed by the entrance-surface-side photodetector element. For example, when the object is formed of a lightweight atom, the radiation transmitted by the object can be absorbed by the entrance-surface-side photodetector element. As described above, the conventional apparatus has the problem that the radiation transmitted by the object is affected by the entrance-surface-side photodetector element.

It is therefore an object of the present invention to provide a radiation image acquisition device capable of acquiring radiation images in different energy bands while reducing the influence on the radiation transmitted by the object.

Solution to Problem

A radiation image acquisition device according to one aspect of the present invention includes: a radiation source which emits radiation; a wavelength conversion member of a flat plate shape which generates scintillation light according to incidence of the radiation emitted from the radiation source and transmitted by an object; first imaging means which condenses and images the scintillation light emitted from an entrance surface for the radiation in the wavelength conversion member in a direction inclined with respect to a direction of a normal to the entrance surface; and second imaging means which condenses and images the scintillation light emitted from a surface opposite to the entrance surface in the wavelength conversion member in a direction inclined with respect to a direction of a normal to the opposite surface.

In the radiation image acquisition device according to the one aspect of the present invention, the first imaging means and the second imaging means condense and image the respective scintillation light beams emitted from the entrance surface for the radiation and from the opposite surface behind it in the wavelength conversion member. This realizes dual-energy imaging to acquire radiation images in different energy bands. In this connection, the first imaging means is arranged at a position apart from the wavelength conversion member, in order to condense the scintillation light emitted from the entrance surface. Therefore, the radiation image acquisition device can have the configuration wherein no imaging means is interposed between the object and the wavelength conversion member, thereby avoiding an incident such that the imaging means affects the radiation transmitted by the object. Accordingly, it is feasible to reduce the influence on the radiation transmitted by the object. Furthermore, the scintillation light to be condensed by the first imaging means is emitted in the direction inclined with respect to the direction of the normal to the entrance surface and the scintillation light to be condensed by the second imaging means is emitted in the direction inclined with respect to the direction of the normal to the opposite surface; for this reason, the same perspective is made in both of the radiation images taken by the two imaging means. Therefore, it becomes easier to perform an operation such as a correction between the images on the entrance surface side and on the opposite surface side.

The radiation image acquisition device may be configured in a mode such that each of the first imaging means and the second imaging means has: a condensing lens unit for condensing the scintillation light emitted from the wavelength conversion member; and an imaging unit for imaging the scintillation light thus condensed. In this case, the scintillation light is condensed with focus on each of the entrance surface and the opposite surface of the wavelength conversion member, which enables acquisition of bright radiation images with good energy separation.

The radiation image acquisition device may be configured in a mode such that the first imaging means and the second imaging means are arranged in plane symmetry with respect to the wavelength conversion member. In this case, the same perspective is made in the radiation image taken by the first imaging means and the radiation image taken by the second imaging means. Therefore, the operation between the images on the entrance surface side and on the opposite surface side requires no operation to invert and correct an image, which further facilitates the operation.

The radiation image acquisition device may be configured in a mode such that an angle of inclination to the direction of the normal to the entrance surface, of the scintillation light to be condensed by the first imaging means is different from an angle of inclination to the direction of the normal to the opposite surface, of the scintillation light to be condensed by the second imaging means and that the radiation image acquisition device further includes: correction means for correcting at least one of an image taken by the first imaging means and an image taken by the second imaging means. In this case, the radiation image taken by the first imaging means and the radiation image taken by the second imaging means have their respective perspectives different from each other. The correction means herein corrects for the perspective of at least one of the images so as to match perspective levels of the two images, thereby realizing high-accuracy dual-energy imaging.

The radiation image acquisition device may be configured in a mode such that the object is a semiconductor device and that the radiation image acquisition device is applied to a semiconductor failure inspection device an inspection target of which is the semiconductor device. In this case, since the radiation transmitted by the semiconductor device as the inspection target is not cut by the imaging unit (imaging device for acquisition of image), the inspection device can detect a failure or the like of the semiconductor device with high accuracy.

Advantageous Effect of Invention

The one aspect of the present invention enables the acquisition of radiation images in different energy bands and the reduction of the influence on the radiation transmitted by the object.

DESCRIPTION OF EMBODIMENTS

Embodiments of the present invention will be described below in detail with reference to the drawings. Identical or equivalent portions will be denoted by the same reference signs in the description of the drawings, without redundant description. It is noted that each drawing is prepared by way of illustration only and is depicted so as to emphasize each part as object of description in particular. For this reason, the dimensional ratios of respective members in the drawings are not always coincident with actual ones.

Figure 1:
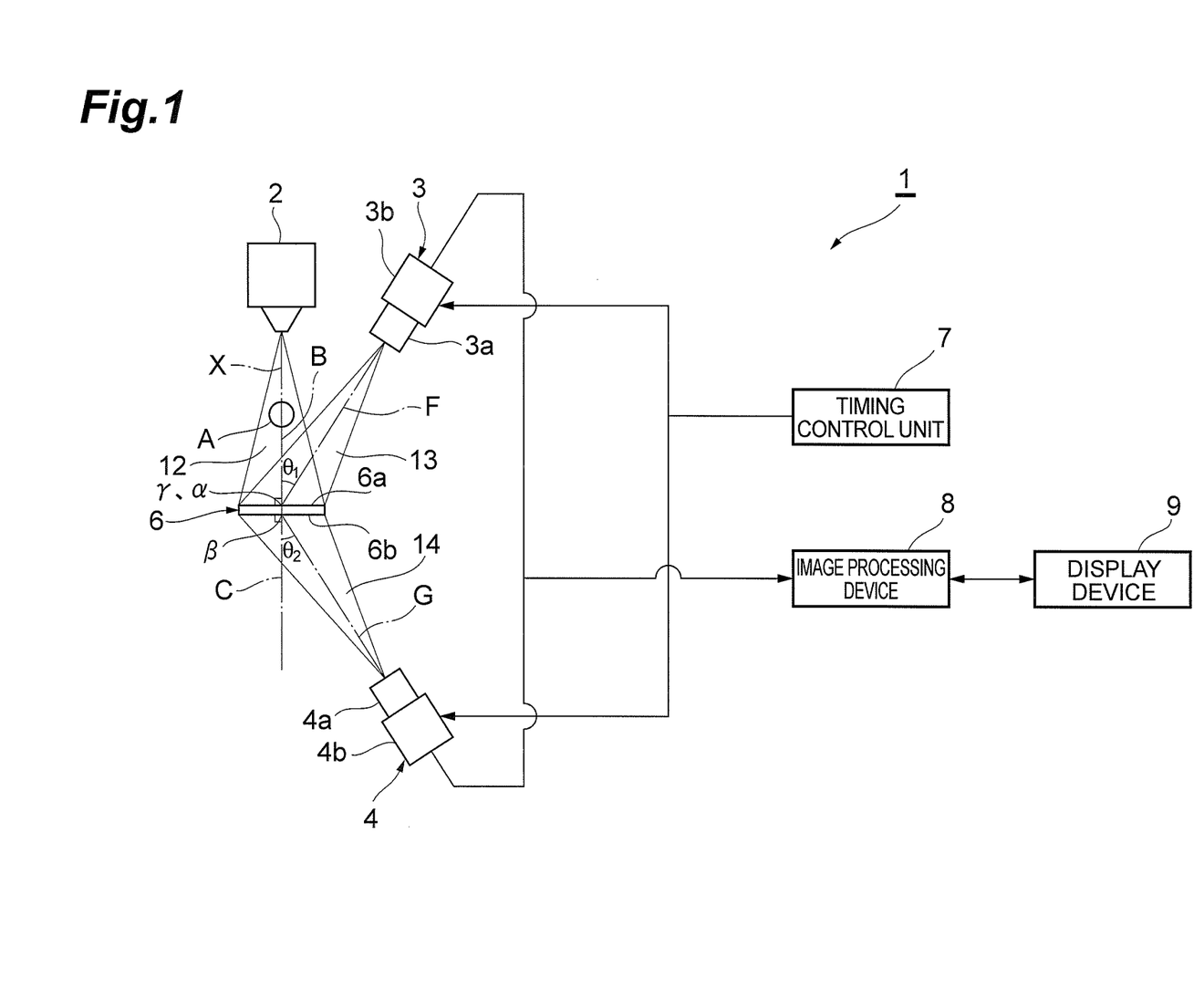
FIG. 1 is a front view of the radiation image acquisition device according to the first embodiment of the present invention.

As shown in FIG. 1, the radiation image acquisition device 1 is a device for acquiring a radiation image of an object A, e.g., an electronic component such as a semiconductor device, or a foodstuff. The radiation image acquisition device 1 is provided with a radiation source 2 which emits radiation such as white X-rays toward the object A, a wavelength conversion plate 6 which generates scintillation light according to incidence of the radiation transmitted by the object A after emitted from the radiation source 2, a front observation photodetector 3 which condenses and images the scintillation light emitted from an entrance surface 6a for the radiation in the wavelength conversion plate 6, and a back observation photodetector 4 which condenses and images the scintillation light emitted from a back surface 6b being a surface opposite to the entrance surface 6a. These radiation source 2, wavelength conversion plate 6, front observation photodetector 3, and back observation photodetector 4 are housed in a housing not shown and fixed in the housing.

The wavelength conversion plate 6 is a wavelength conversion member of a flat plate shape, e.g., a scintillator of any one of $Gd_2O_2S:Tb$, $Gd_2O_2S:Pr$, $CsI:Tl$, $CdWO_4$, $CaWO_4$, $Gd_2SiO_5:Ce$, $Lu_{0.4}Gd_{1.6}SiO_5$, $Bi_4Ge_3O_{12}$, $Lu_2SiO_5:Ce$, $Y_2SiO_5$, $YAlO_3:Ce$, $Y_2O_2S:Tb$, $YTaO_4:Tm$, and so on. The thickness of the wavelength conversion plate 6 is set to an appropriate value depending upon a radiation energy band detected, in the range of several μm to several mm.

The front observation photodetector 3 (which will be referred to hereinafter as "front detector 3") is an imaging means of an indirect conversion method that photographs a projection image (radiation transmission image) of the object A projected on the wavelength conversion plate 6, from the entrance surface 6a side of the wavelength conversion plate 6. The front detector 3 is a detector of a lens coupling type having a condensing lens unit 3a for condensing the scintillation light emitted from the entrance surface 6a of the wavelength conversion plate 6, and an imaging unit 3b for imaging the scintillation light condensed by the condensing lens unit 3a. The condensing lens unit 3a condenses the scintillation light in a front detector field 13. The imaging unit 3b to be used herein is, for example, a CMOS sensor, a CCD sensor, or the like.

The back observation photodetector 4 (which will be referred to hereinafter as "back detector 4") is an imaging means of the indirect conversion method that photographs the projection image (radiation transmission image) of the object A projected on the wavelength conversion plate 6, from the back surface 6b side of the wavelength conversion plate 6. The back detector 4 is a detector of the lens coupling type having a condensing lens unit 4a for condensing the scintillation light emitted from the back surface 6b of the wavelength conversion plate 6, and an imaging unit 4b for imaging the scintillation light condensed by the condensing lens unit 4a, and thus it has the same configuration as the aforementioned front detector 3. The condensing lens unit 4a condenses the scintillation light in a back detector field 14. The imaging unit 4b to be used herein is, for example, a CMOS sensor, a CCD sensor, or the like.

Furthermore, the radiation image acquisition device 1 is provided with a timing control unit 7 for controlling imaging timing at the front detector 3 and at the back detector 4, an image processing device 8 for receiving input image signals from the front detector 3 and from the back detector 4 and executing a predetermined processing procedure such as image processing based on each of the input image signals, and a display device 9 for receiving an input image signal from the image processing device 8 and displaying a radiation image. The timing control unit 7 and the image processing device 8 are composed of a computer having a CPU (Central Processing Unit), a ROM (Read Only Memory), a RAM (Random Access Memory), input/output interfaces, and so on. The display device 9 to be used herein is a well-known display. The timing control unit 7 and the image processing device 8 may be configured as a program executed by a single computer or as respective units provided individually.

The below will describe the positional relationship among the aforementioned radiation source 2, wavelength conversion plate 6, front detector 3, and back detector 4. As shown in FIG. 1, the radiation source 2 is arranged so that an optical axis X of the radiation coincides with a normal B to the entrance surface 6a of the wavelength conversion plate 6. Namely, the radiation source 2 faces the object A and the entrance surface 6a and is arranged on the normal B to the entrance surface 6a. The optical axis X of the radiation herein is a straight line connecting a radiation emission point of the radiation source 2 and an arbitrary point γ on the entrance surface 6a of the wavelength conversion plate 6. In the present embodiment, the arbitrary point γ is set to be a central point of the entrance surface 6a and in this case, the radiation is radiated with little relative unevenness. The normal B here is a straight line extending normally to the entrance surface 6a from an arbitrary point α on the entrance surface 6a. In the present embodiment, the arbitrary point α is set to be the central point of the entrance surface 6a and thus the optical axis X of the radiation and the normal B coincide with each other. It is a matter of course that the arbitrary point γ and the arbitrary point α do not have to be coincident with the central point of the entrance surface 6a.

The front detector 3 is arranged so that an optical axis F of the incorporated condensing lens unit 3a makes a predetermined angle $\theta_1$ with respect to the normal B to the entrance surface 6a, so as to be able to image the scintillation light emitted from the entrance surface 6a of the wavelength conversion plate 6. Namely, the front detector 3 faces the entrance surface 6a and is arranged at a position off the normal B to the entrance surface 6a. This condensing lens unit 3a focuses on the entrance surface 6a and condenses the scintillation light emitted in a direction (inclined direction) at the angle $\theta_1$ to the normal B from the entrance surface 6a, toward the imaging unit 3b. This condensing lens unit 3a to be used herein can be a shift lens or a tilt lens.

As described above, the front detector 3 is arranged off the optical axis X of the radiation source 2. Namely, the front detector 3 is arranged so as to be located apart from an emission region of the radiation from the radiation source 2 (which is a region where a radiation beam 12 exists). This arrangement prevents the front detector 3 from being exposed to the radiation from the radiation source 2 and prevents a direct conversion signal of radiation from being produced inside the front detector 3 to generate noise.

The back detector 4 is arranged so that an optical axis G of the incorporated condensing lens unit 4a makes a predetermined angle $\theta_2$ with respect to a normal C to the back surface 6b, so as to be able to image the scintillation light emitted from the back surface 6b of the wavelength conversion plate 6. Namely, the back detector 4 faces the back surface 6b and is arranged at a position off the normal C to the back surface 6b. The normal C here is a straight line extending normally to the back surface 6b from an arbitrary point β on the back surface 6b. Particularly, in the present embodiment, the arbitrary point β is set at a central point of the back surface 6b, the arbitrary point α on the entrance surface 6a and the arbitrary point β on the back surface 6b are located on the same straight line, and this straight line is coincident with the normal B and the normal C. The condensing lens unit 4a focuses on the back surface 6b and condenses the scintillation light emitted in a direction (inclined direction) at the angle $\theta_2$ to the direction of the normal C from the back surface 6b, toward the imaging unit 4b.

It is noted herein that in the radiation image acquisition device 1, the angle $\theta_1$ and the angle $\theta_2$ are set equal to each other. The optical axis X of the radiation source 2, the optical axis F of the front detector 3, and the optical axis G of the back detector 4 are located on the same plane and, the optical axis F of the front detector 3 and the optical axis G of the back detector 4 are located on the same side with respect to the normals B, C. An optical path length from the entrance surface 6a of the wavelength conversion plate 6 to the front detector 3 can be set equal to an optical path length from the back surface 6b of the wavelength conversion plate 6 to the back detector 4. The front detector 3 and the back detector 4 can be arranged in plane symmetry with respect to the wavelength conversion plate 6.

The following will describe the operation of the radiation image acquisition device 1 having the above-described configuration. First, the timing control unit 7 performs control to make the front detector 3 and the back detector 4 simultaneously carry out their respective imaging operations. The imaging of radiation transmission images of the object A in different energy bands can be implemented based on the imaging timing control by the timing control unit 7. In more detail, the front detector 3 acquires the radiation transmission image in a relatively low energy band and the back detector 4 the radiation transmission image in a relatively high energy band. This operation realizes dual-energy imaging. It is noted that the radiation image acquisition device 1 is configured to allow control to make the imaging times of the front detector 3 and the back detector 4 different from each other. The device may also be configured to control the front detector 3 and the back detector 4 to different exposure times and/or different numbers of photos taken thereby.

The functions of the front detector 3 and the back detector 4 will be specifically described in more detail. The front detector 3 detects fluorescence (scintillation light) resulting from conversion on the side relatively near the entrance surface 6a. The detection of the fluorescence resulting from the conversion on the entrance surface 6a side is characterized by little blurring of fluorescence and high luminance of fluorescence. This is because the front observation can be less affected by diffusion and self-absorption inside the wavelength conversion plate 6. On the other hand, the back detector 4 detects fluorescence resulting from conversion on the side relatively near the back surface 6b of the wavelength conversion plate 6. In this case as well, the observation can be less affected by diffusion and self-absorption inside the wavelength conversion plate 6.

Next, the front detector 3 and the back detector 4 output their respective image signals corresponding to the radiation images on both of the front and back surfaces, to the image processing device 8. When the image processing device 8 receives the respective input image signals from the front detector 3 and from the back detector 4, the image processing device 8 executes the predetermined processing such as an inter-image operation, e.g., a differential operation or an addition operation, based on the input image signals, and outputs an image signal after the image processing to the display device 9. When the display device 9 receives the input image signal after the image processing from the image processing device 8, the display device 9 displays a radiation image according to the input image signal after the image processing.

Figure 2:
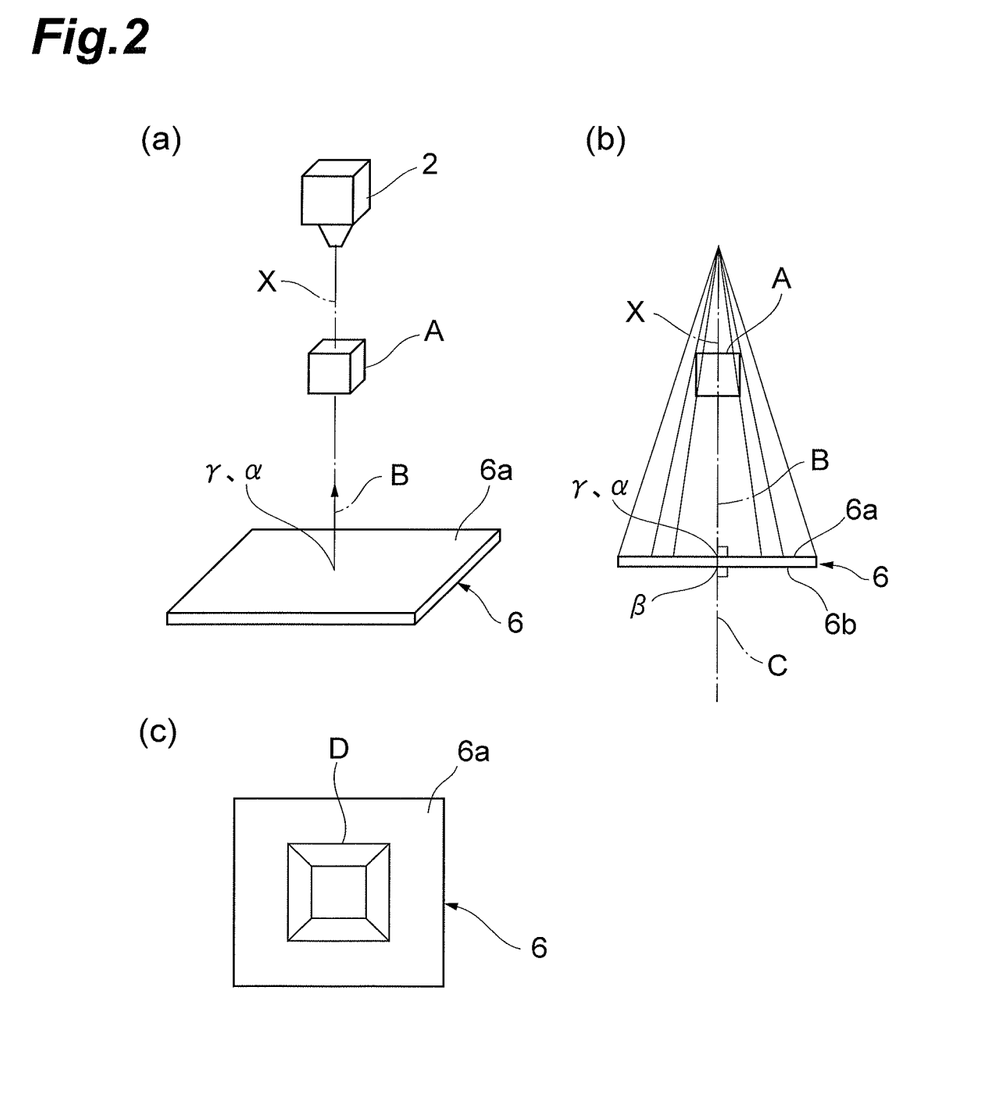
FIG. 2 is an explanatory drawing for explaining a projection image in the radiation image acquisition device shown in FIG. 1.

FIG. 2(a) is a perspective view showing the positional relationship among the radiation source 2, object A, and wavelength conversion plate 6 in the radiation image acquisition device 1, FIG. 2(b) a front view showing the positional relationship among the radiation source 2, object A, and wavelength conversion plate 6, and FIG. 2(c) a plan view showing a projection image D of the object A projected on the wavelength conversion plate 6. FIG. 2 shows a situation in which the object A is of a 3D shape, for easier understanding. When the radiation source 2 is arranged on the normal B to the entrance surface 6a and the optical axis X of the radiation coincides with the normal B to the entrance surface 6a as shown in FIG. 2(a), no perspective is made in the projection image D onto the entrance surface 6a, as shown in FIG. 2(c).

FIG. 3(a) is a plan view showing the projection image D projected on the entrance surface 6a in the radiation image acquisition device 1, FIG. 3(b) a perspective view showing the positional relationship among the front detector 3, back detector 4, and wavelength conversion plate 6, FIG. 3(c) a drawing showing a front-side image Pa acquired by the front detector 3 and fed to the image processing device 8, and FIG. 3(d) a drawing showing a back-side image Pb acquired by the back detector 4 and fed to the image processing device 8.

Figure 3:
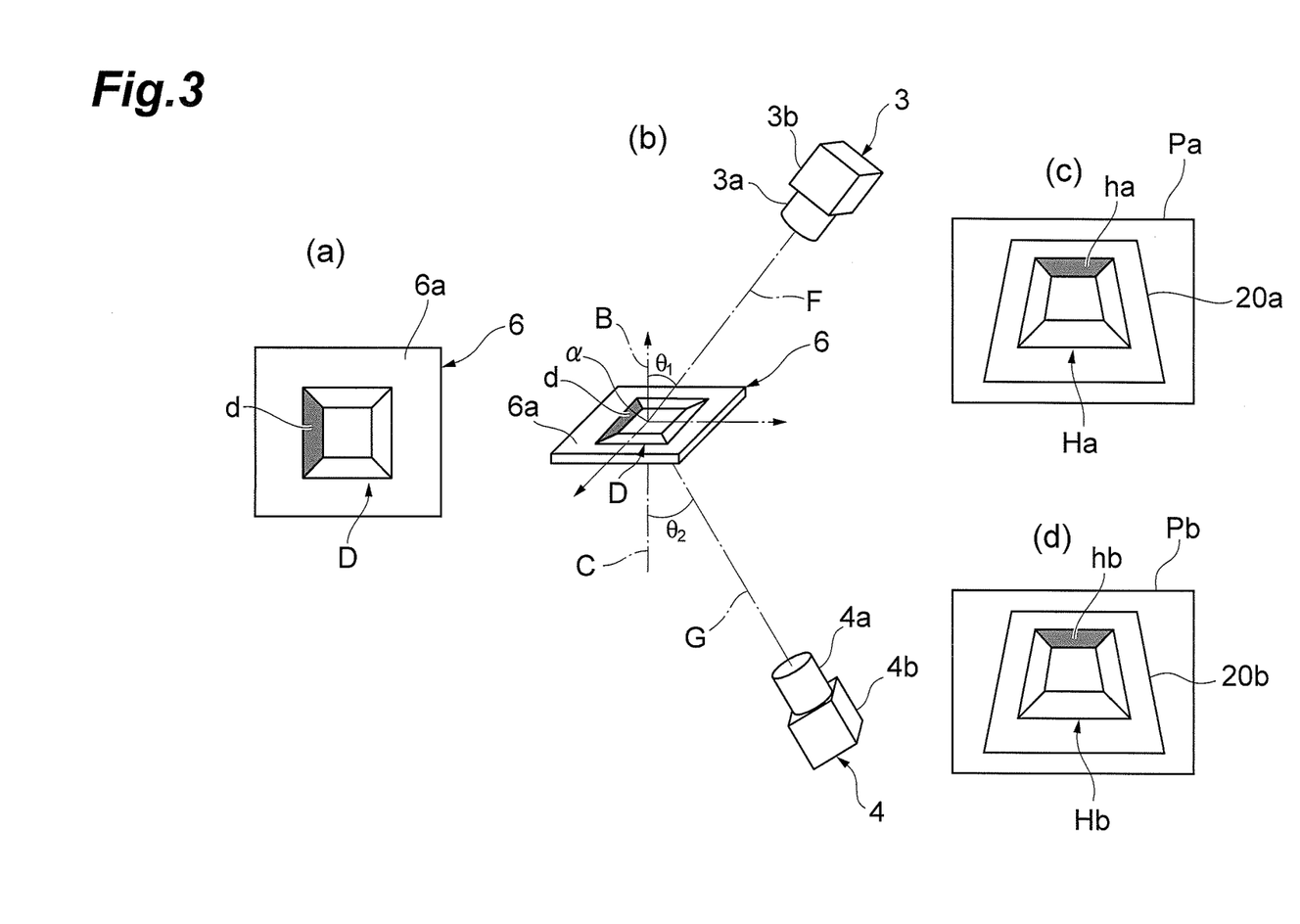
FIG. 3 is an explanatory drawing for explaining perspectives of images in the radiation image acquisition device shown in FIG. 1.

The below will describe a case where a part of the projection image D is a feature part d (a colored portion corresponding to a side face of the object A, in the example of FIG. 3). When the optical axis F of the front detector 3 and the optical axis G of the back detector 4 make their respective angles $\theta_1$, $\theta_2$ equal to each other with respect to the normals B, C as shown in FIG. 3(b), the same perspective is made in the front-side images Pa, Pb, as shown in FIG. 3(c), (d). Namely, a front-side wavelength-conversion-plate image 20a, a front-side object image Ha, and a front-side feature-part image ha included in the front-side image Pa are approximately identical in position, size, and shape to a back-side wavelength-conversion-plate image 20b, a back-side object image Hb, and a back-side feature-part image hb included in the back-side image Pb. The front-side image Pa and the back-side image Pb have the perspective such that the feature part d is more reduced than the other portions, and directions of occurrence of the perspective about the object A are identical. These are mutually inverted images.

In this case, the inter-image operation by the image processing device 8 is carried out to match the images Pa, Pb on both of the front and back surfaces, without execution of a perspective correction of the front-side image Pa and the back-side image Pb. Another available method is such that the inter-image operation by the image processing device 8 is to correct for the two perspectives of the front-side image Pa and the back-side image Pb to obtain a front-side image and a back-side image without a perspective. In this case, correction amounts for the perspective of the front-side image Pa and for the perspective of the back-side image Pb are equal.

In the radiation image acquisition device 1 of the present embodiment described above, the front detector 3 and the back detector 4 condense and image the respective scintillation light beams emitted from the entrance surface 6a and the back surface 6b of the wavelength conversion plate 6, thereby realizing the dual-energy imaging to acquire radiation images in different energy bands. In this configuration, the front detector 3 is arranged at the position apart from the wavelength conversion plate 6, without any detector interposed between the object A and the wavelength conversion plate 6. This configuration permits the device to avoid the incident that the imaging means affects the radiation transmitted by the object A. Therefore, the influence on the radiation transmitted by the object A is reduced and the radiation in a low energy band is suitably detected. In other words, no shadow of detector is cast on the radiation transmission images, so as to suppress generation of noise component and cause no attenuation of radiation due to the detector, thus suppressing reduction of signal components. As a result, it becomes feasible to make a difference between the low energy band and the high energy band in the dual-energy imaging larger and to exhibit a high energy resolution, allowing achievement of higher contrast. This advantage is prominently demonstrated, particularly, in the case where the object A is formed of silicon or an atom lighter in weight than silicon. Namely, even if the object A is formed of a lightweight atom, the radiation in the low energy band transmitted by the object A is converted into scintillation light, without being absorbed or attenuated, and this light is imaged by the front detector 3; therefore, the radiation image in the low energy band can be acquired with accuracy. Furthermore, the low-energy image and the high-energy image can be simultaneously acquired by a single imaging operation, so as to ensure simultaneity, reduce an exposure dose, and avoid pixel shifts (misregistration). The dual-energy imaging can be realized even by means of the single wavelength conversion plate 6. In addition, since the scintillation light to be condensed by the front detector 3 is emitted in the direction at the angle $\theta_1$ to the direction of the normal B to the entrance surface 6a and the scintillation light to be condensed by the back detector 4 is emitted in the direction at the angle $\theta_2$ to the direction of the normal C to the back surface 6b, the same perspective is made in the radiation images Pa, Pb, which facilitates the operation between the images on the entrance surface 6a side and on the back surface 6b side. Furthermore, the entire device is constructed in a more compact scale than the device is constructed with the front detector 3 and the back detector 4 being arranged on the normals B, C.

When white X-rays are used as the radiation, the low-energy image and the high-energy image can also be simultaneously acquired by a single imaging operation of white X-rays, so as to ensure simultaneity, reduce an exposure dose, and avoid pixel shifts (misregistration).

As the condensing lens unit 3a and the condensing lens unit 4a condense the light with focus on each of the entrance surface 6a and the back surface 6b of the wavelength conversion plate 6, bright radiation images can be acquired with good energy separation.

Since the front detector 3 and the back detector 4 are arranged in plane symmetry with respect to the wavelength conversion plate 6, the same perspective is made in the front-side image Pa and the back-side image Pb and the directions of occurrence of the perspective about the object A are also identical. Therefore, the inter-image operation between the front-side image Pa and the back-side image Pb requires no operation to invert and correct an image, which further facilitates the operation.

Figure 4:
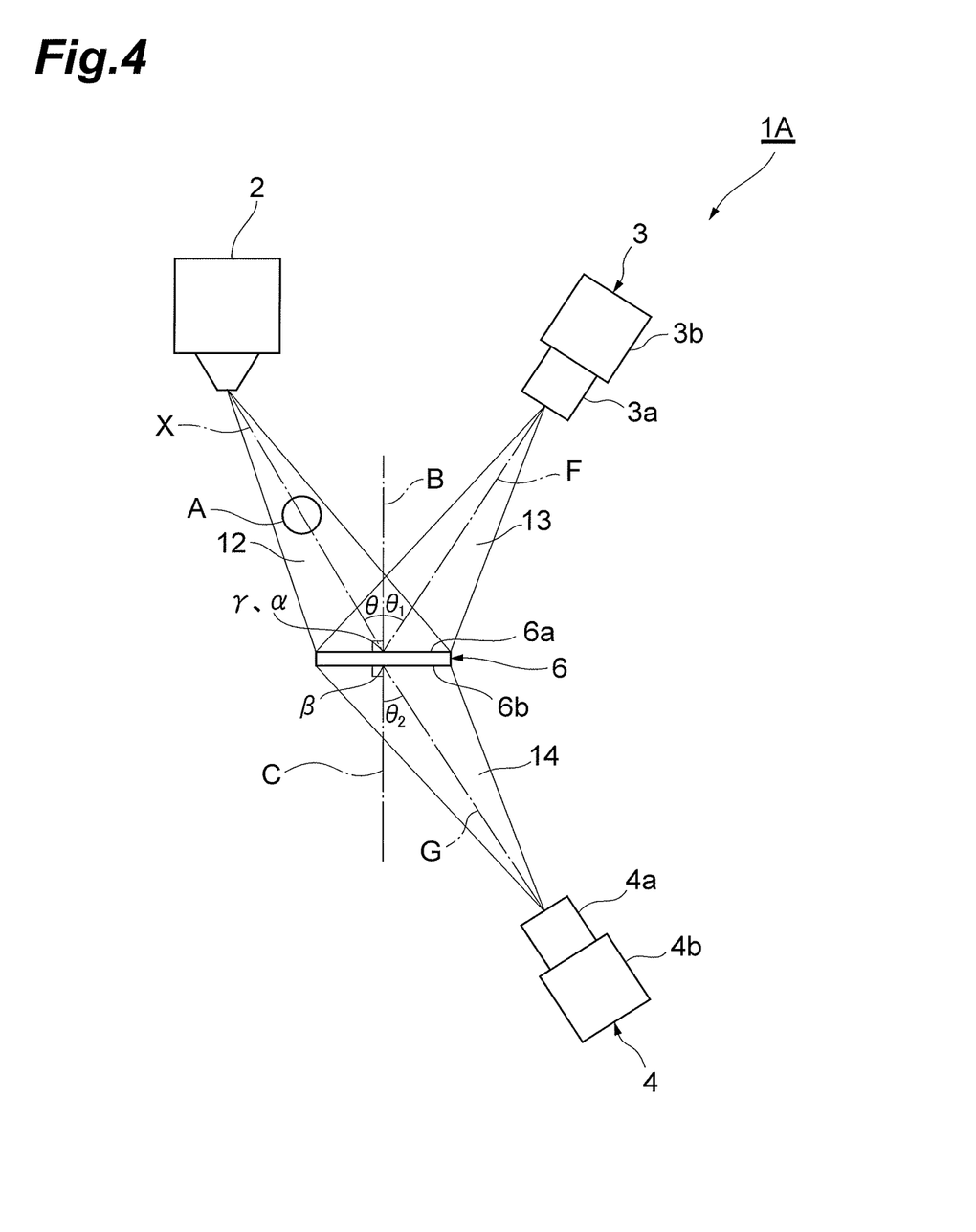
FIG. 4 is a front view Of the radiation image acquisition device according to the second embodiment of the present invention.
Figure 6:
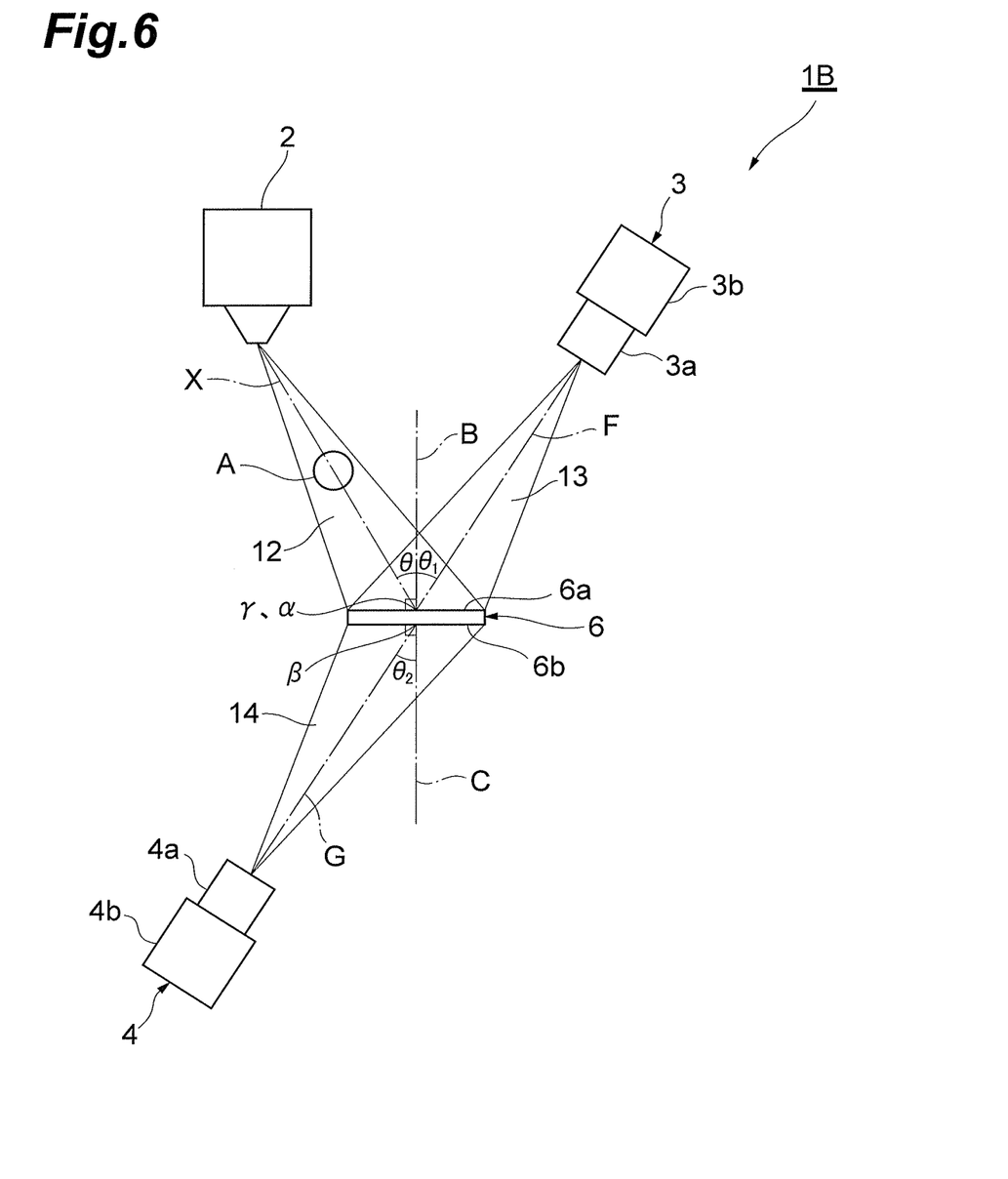
FIG. 6 is a front view of the radiation image acquisition device according to the third embodiment of the present invention.

FIG. 4 is a front view of the radiation image acquisition device according to the second embodiment. The radiation image acquisition device 1A shown in FIG. 4 is different from the radiation image acquisition device 1 of the first embodiment shown in FIG. 1 in that the radiation source 2 is arranged so that the optical axis X of the radiation makes a predetermined angle θ with respect to the normal B to the entrance surface 6a of the wavelength conversion plate 6. More specifically, the radiation source 2 is arranged so that the optical axis X of the radiation and the optical axes F, G of the condensing lens units 3a, 4a are located on the same plane and on the sides opposite to each other with respect to the normals B, C. It is noted herein that the arbitrary point γ and the arbitrary point α do not have to be the central point of the entrance surface 6a and do not have to be the same point, either. FIG. 4 is depicted without illustration of the timing control unit 7, image processing device 8, and display device 9. FIG. 6 is also depicted similarly without illustration of these components.

In the radiation image acquisition device 1A, the front detector 3 is also arranged apart from the radiation emission region from the radiation source 2 (the region where the radiation beam 12 exists). This arrangement prevents the front detector 3 from being exposed to the radiation from the radiation source 2 and thus prevents a direct conversion signal of radiation from being produced inside the front detector 3 to generate noise.

Figure 5:
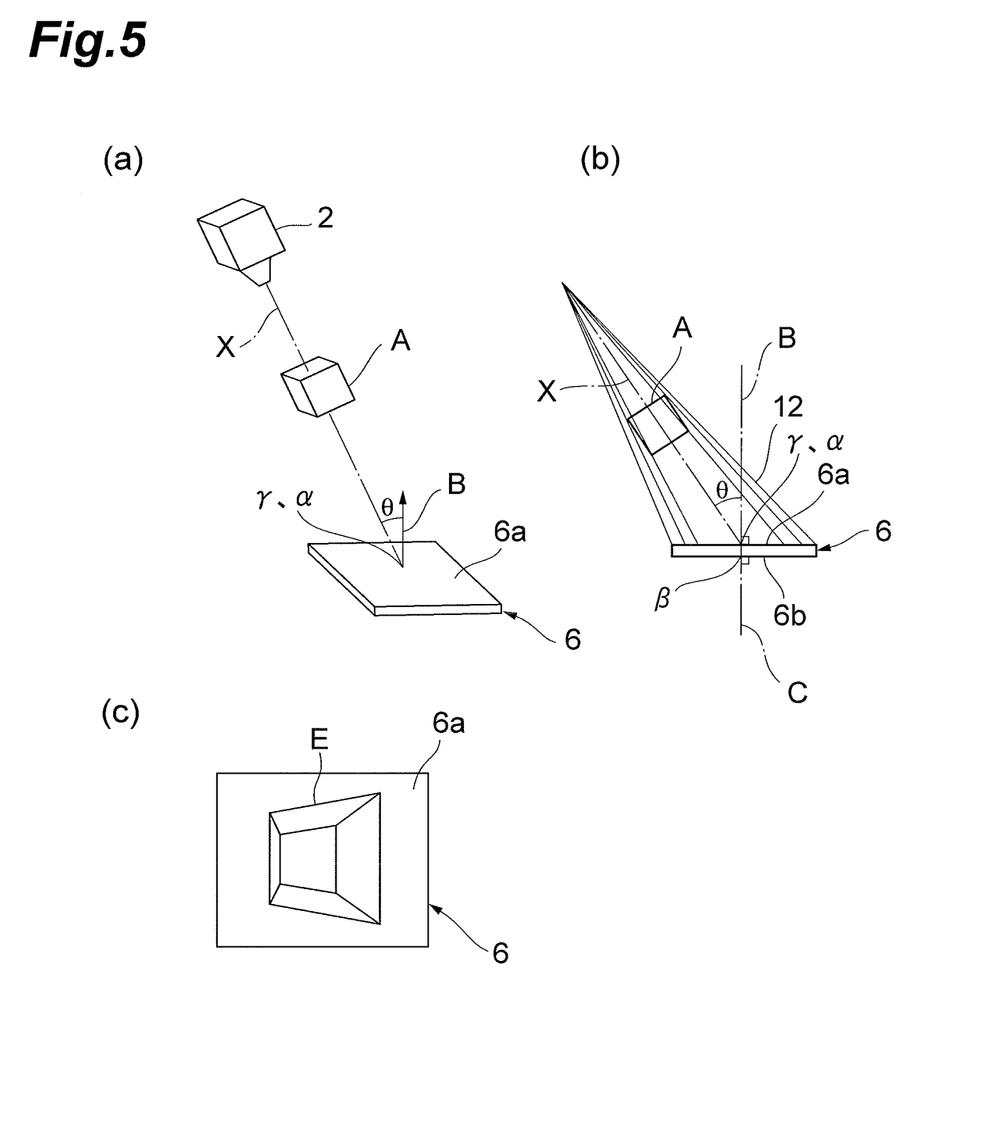
FIG. 5 is an explanatory drawing for explaining a perspective of a projection image in the radiation image acquisition device shown in FIG. 4.

FIG. 5(a) is a perspective view showing the positional relationship among the radiation source 2, object A, and wavelength conversion plate 6 in the radiation image acquisition device 1B, FIG. 5(b) a front view showing the positional relationship among the radiation source 2, object A, and wavelength conversion plate 6, and FIG. 5(c) a plan view showing a projection image E of the object A projected on the wavelength conversion plate 6. FIG. 5 shows a situation in which the object A is of a 3D shape, for easier understanding. When the radiation source 2 is arranged at the position off the normal B to the entrance surface 6a and the optical axis X of the radiation makes the predetermined angle θ with respect to the normal B to the entrance surface 6a as shown in FIG. 5(a), a perspective is made in the projection image E onto the entrance surface 6a, as shown in FIG. 5(c). This perspective of the projection image E is corrected according to needs by the image processing device 8. Although FIG. 5(a) shows that the main body of the radiation source 2 is parallel to the optical axis X, for convenience' sake of explanation, the orientation of arrangement of the radiation source 2 can be optionally set according to the layout of the device.

The radiation image acquisition device 1A achieves the same operational effect as the radiation image acquisition device 1 does.

FIG. 6 is a front view of the radiation image acquisition device according to the third embodiment. The radiation image acquisition device 1B shown in FIG. 6 is different from the radiation image acquisition device 1A of the second embodiment shown in FIG. 4 in that the back detector 4 is not arranged in plane symmetry to the front detector 3 with respect to the wavelength conversion plate 6 and the optical axis F and the optical axis G are located on the sides opposite to each other with respect to the normals B, C. Namely, the back detector 4 is arranged so that the optical axis G of the condensing lens unit 4a and the optical axis X of the radiation source 2 are located on the same side with respect to the normals B, C.

In the radiation image acquisition device 1B, different perspectives are made in the front-side image acquired by the front detector 3 and in the back-side image acquired by the back detector 4. Therefore, the inter-image operation by the image processing device 8 is to correct for the perspectives of the front-side image and the back-side image.

The radiation image acquisition device 1B reduces the influence on the radiation transmitted by the object A and suitably detects the radiation in the low energy band as the radiation image acquisition devices 1 and 1A do.

Figure 7:
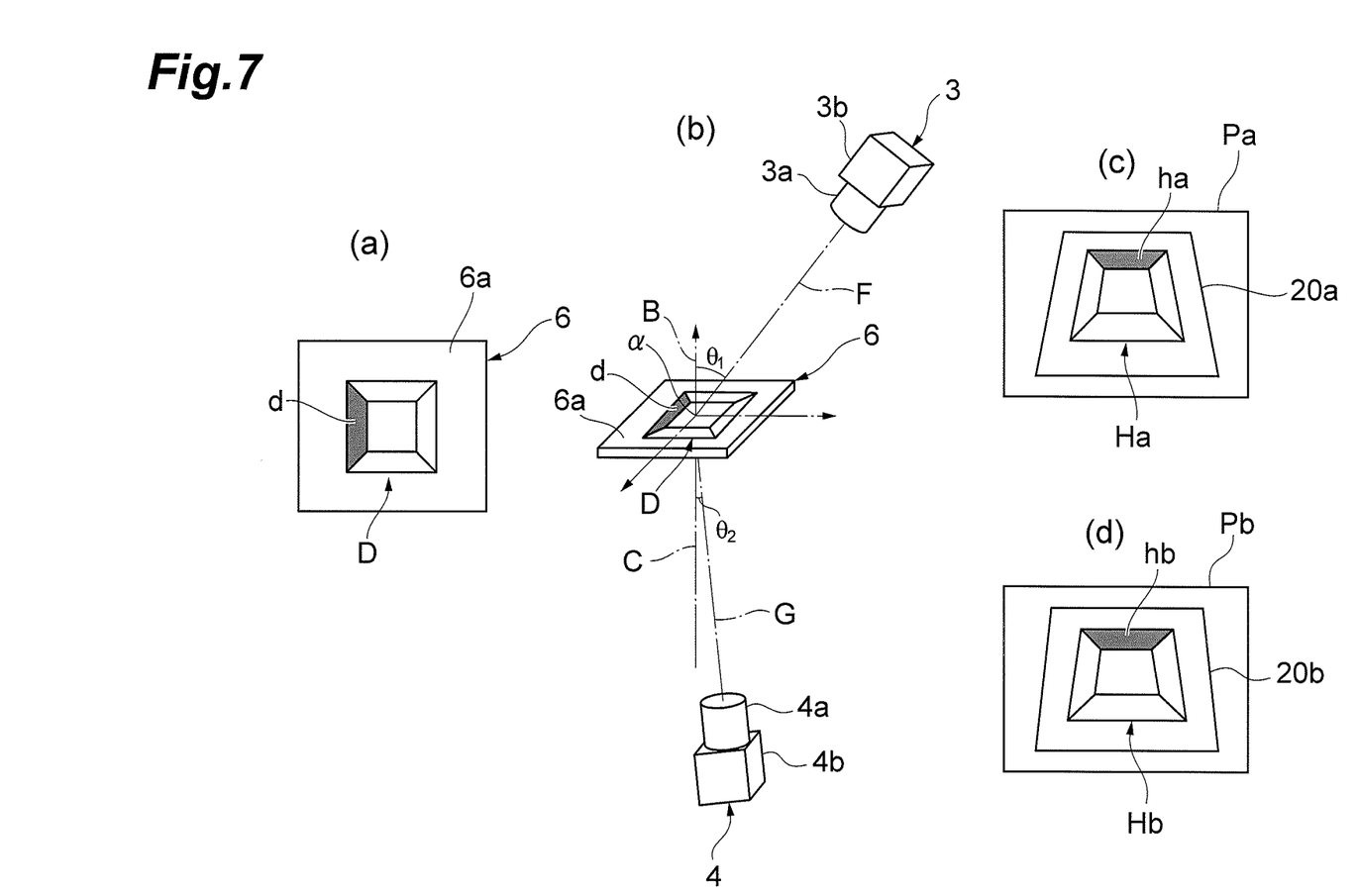
FIG. 7 is an explanatory drawing for explaining perspectives of images in the radiation image acquisition device which is a modification example of the present invention.

The above described the embodiments of the present invention but the present invention is by no means intended to be limited to the above embodiments. For example, the above embodiments described the examples wherein the angle $θ_1$ and the angle $θ_2$ were equal, but the angle $θ_1$ and the angle $θ_2$ may be different from each other, as shown in FIG. 7(b). In this case, as shown in FIG. 7(c), (d), amounts of perspectives are different between the front-side image Pa and the back-side image Pb, but the image processing device 8 functions as a correction means to correct for at least one of the perspectives of the front-side image Pa and the back-side image Pb so as to match the perspective amounts of the two images, thereby realizing high-accuracy dual-energy imaging. For example, as shown in FIG. 7, the perspective amount of the front-side image Pa taken by the front detector 3 with the larger inclination angle is larger than that of the back-side image Pb, and in this case, the front-side image Pa is corrected to obtain a front-side image matched with the back-side image Pb. Another available method is such that the two perspectives of the front-side image Pa and the back-side image Pb are corrected to obtain a front-side image and a back-side image without a perspective.

The radiation source 2, front detector 3, and back detector 4 do not always have to be limited to the configuration wherein the optical axis X, the optical axis F, and the optical axis G are arranged on the same plane, but they may also be three-dimensionally arranged according to circumstances around the axis along the directions of the normals B, C.

The above embodiments used the lens coupling type detectors as detectors, but the condensing lens unit and the imaging unit may be provided as separate members.

An effective application is such that the object A is a semiconductor device and the radiation image acquisition device of the above embodiment is applied to a semiconductor failure inspection device an inspection target of which is the semiconductor device. In this case, the radiation transmitted by the semiconductor device as the inspection target is not cut by the imaging unit (imaging device for acquisition of image) and thus a failure or the like of the semiconductor device can be detected with accuracy.

INDUSTRIAL APPLICABILITY

The one aspect of the present invention enables the acquisition of radiation images in different energy bands and the reduction of the influence on the radiation transmitted by the object.

REFERENCE SIGNS LIST 1, 1A, 1B radiation image acquisition devices; 2 radiation source; 3 front observation photodetector (first imaging means); 3a condensing lens unit; 3b imaging unit; 4 back observation photodetector (second imaging means); 4a condensing lens unit; 4b imaging unit; 6 wavelength conversion plate (wavelength conversion member); 6a entrance surface; 6b back surface (opposite surface); 8 image processing device (correction means); A object; B normal to entrance surface; C normal to back surface.

The invention claimed is:

1. A radiation image acquisition device comprising:
a radiation source configured to emit radiation;
a wavelength conversion member of a flat plate shape configured to generate scintillation light according to incidence of the radiation emitted from the radiation source and transmitted by an object;
first imaging means configured to condense and image the scintillation light emitted from an entrance surface for the radiation in the wavelength conversion member in a direction inclined with respect to a direction of a normal to the entrance surface; and
second imaging means configured to condense and image the scintillation light emitted from a surface opposite to the entrance surface in the wavelength conversion member in a direction inclined with respect to a direction of a normal to the opposite surface,
wherein a condensing lens unit of the first imaging means is configured to focus on the entrance surface and condense the scintillation light emitted in the direction inclined with respect to the normal to the entrance surface from the entrance surface toward an imaging unit, and
wherein a condensing lens unit of the second imaging means is configured to focus on the opposite surface and condense the scintillation light emitted in the direction inclined with respect to the normal to the opposite surface from the opposite surface toward an imaging unit.

2. The radiation image acquisition device according to claim 1,
wherein each of the first imaging means and the second imaging means has:
a condensing lens unit configured to condense the scintillation light emitted from the wavelength conversion member; and
an imaging unit configured to image the scintillation light thus condensed.

3. The radiation image acquisition device according to claim 1,
wherein an angle of inclination with respect to the direction of the normal to the entrance surface of the scintillation light condensed by the first imaging means and an angle of inclination with respect to the direction of the normal to the opposite surface of the scintillation light condensed by the second imaging means are equal to one another.

4. The radiation image acquisition device according to claim 3,
wherein the radiation source is arranged on the normal to the entrance surface.

5. The radiation image acquisition device according to claim 3,
wherein the radiation source is arranged so that an optical axis of the radiation makes a predetermined angle with respect to the normal to the entrance surface.

6. The radiation image acquisition device according to claim 1,
wherein the first imaging means and the second imaging means are arranged in plane symmetry with respect to the wavelength conversion member.

7. The radiation image acquisition device according to claim 6,
wherein the radiation source is arranged on the normal to the entrance surface.

8. The radiation image acquisition device according to claim 6,
wherein the radiation source is arranged so that an optical axis of the radiation makes a predetermined angle with respect to the normal to the entrance surface.

9. The radiation image acquisition device according to claim 1,
wherein an optical axis of the condensing lens unit of the first imaging means and an optical axis of the condensing lens unit of the second imaging means are positioned on opposite sides from one another, with the normal to the entrance surface and the normal to the opposite surface as references.

10. The radiation image acquisition device according to claim 9,
wherein the radiation source is arranged so that an optical axis of the radiation makes a predetermined angle with respect to the normal to the entrance surface.

11. The radiation image acquisition device according to claim 1,
wherein an angle of inclination to the direction of the normal to the entrance surface, of the scintillation light to be condensed by the first imaging means is different from an angle of inclination to the direction of the normal to the opposite surface, of the scintillation light to be condensed by the second imaging means,
said radiation image acquisition device further comprising:
correction means configured to correct at least one of an image taken by the first imaging means and an image taken by the second imaging means.

12. The radiation image acquisition device according to claim 1,
wherein the radiation source is arranged on the normal to the entrance surface.

13. The radiation image acquisition device according to claim 1,
wherein the radiation source is arranged so that an optical axis of the radiation makes a predetermined angle with respect to the normal to the entrance surface.

14. The radiation image acquisition device according to claim 1,
wherein an optical path length from the entrance surface to the first imaging means is equal to an optical path length from the opposite surface to the second imaging means.

15. The radiation image acquisition device according to claim 1,
wherein the first and second imaging means are configured so as to perform imaging simultaneously.

16. The radiation image acquisition device according to claim 1,
wherein the object is a semiconductor device,
said radiation image acquisition device being applied to a semiconductor failure inspection device an inspection target of which is the semiconductor device.

17. The radiation image acquisition device according to claim 1,
wherein the object is an electronic component.

* * * * *